(12) United States Patent
Komachi et al.

(10) Patent No.: US 6,970,736 B2
(45) Date of Patent: Nov. 29, 2005

(54) ANALYSIS SYSTEM OF MATTER ADHERED TO INSIDE WALL OF VESSEL

(75) Inventors: Yuichi Komachi, Akishima (JP); Katsuo Aizawa, Yokohama (JP); Atsushi Utsumi, Kawanishi (JP)

(73) Assignee: Machida Endoscope Co., Ltd., Tokyo (JP)

( * ) Notice: Subject to any disclaimer, the term of this patent is extended or adjusted under 35 U.S.C. 154(b) by 515 days.

(21) Appl. No.: 10/045,866

(22) Filed: Oct. 29, 2001

(65) Prior Publication Data

US 2002/0072678 A1  Jun. 13, 2002

(30) Foreign Application Priority Data

Oct. 31, 2000 (JP) ............................. 2000-331737

(51) Int. Cl.$^7$ ............................. A61B 5/02; A61B 6/00; G02B 6/04
(52) U.S. Cl. ............... 600/479; 600/407; 600/476; 385/115; 385/116; 385/120; 385/123
(58) Field of Search ................. 600/475, 477, 600/478, 377, 342, 182; 606/13–17, 7; 385/12, 385/28, 58, 49, 70, 116, 117, 118, 120; 356/301

(56) References Cited

U.S. PATENT DOCUMENTS

| | | | |
|---|---|---|---|
| 4,867,529 A | | 9/1989 | Utsumi et al. ............ 350/96.25 |
| 5,104,392 A | * | 4/1992 | Kittrell et al. ............... 606/15 |
| 5,280,788 A | | 1/1994 | Janes et al. ................ 128/665 |
| 5,293,872 A | * | 3/1994 | Alfano et al. ............... 600/475 |
| 5,402,508 A | * | 3/1995 | O'Rourke et al. ............ 385/31 |
| 5,496,305 A | * | 3/1996 | Kittrell et al. ............... 606/15 |
| 5,710,626 A | * | 1/1998 | O'Rourke et al. .......... 356/301 |
| 5,842,995 A | | 12/1998 | Mahadecan-Jensen et al. ........................... 600/473 |
| 5,953,477 A | | 9/1999 | Wach et al. ................ 385/115 |
| 6,222,970 B1 | * | 4/2001 | Wach et al. ................ 385/115 |
| 6,487,349 B2 | * | 11/2002 | Wach et al. ................ 385/115 |
| 2002/0168317 A1 | * | 11/2002 | Daighighian et al. ....... 424/1.11 |

FOREIGN PATENT DOCUMENTS

| WO | WO 95/11624 A | 5/1995 |
|---|---|---|
| WO | WO 99/65382 A | 12/1999 |

OTHER PUBLICATIONS

"Study of Fiber-optic Probes for *in Vivo* Medical Raman Spectroscopy", M.G. Shim, B.C. Wilson, E. Marple, and M. Wach, Applied Spectroscopy, vol. 53, No. 6, 1999, pp 619-627.

* cited by examiner

*Primary Examiner*—Ali Imam
*Assistant Examiner*—Baisakhi Roy
(74) *Attorney, Agent, or Firm*—Brown & Michaels, PC; Eugene Stephens & Associates

(57) ABSTRACT

An analysis system comprises an endoscope 10 insertable into the vessel and a Raman analysis apparatus 40. An insert cable 54 of the Raman analysis apparatus 40 is inserted into a channel 10a of the endoscope 10. An excitation optical fiber 60 and a bundle 70A of a plural number of light receivingoptical fibers 70 are received in the insert cable 54. A transparent small piece 63 having a film-like excitation optical filter 64 is abutted against the distal end of the fiber 60. A transparent plate 71 having a film-like light reciving optical filter 72 is abutted against the distal end of fibers bundle 70A. The plate 71 has a center hole 71a and the piece 63 is fitted into the hole 71a.

3 Claims, 5 Drawing Sheets

ANALYSIS SYSTEM OF MATTER ADHERED TO INSIDE WALL OF VESSEL

BACKGROUND OF THE INVENTION

This invention relates to a system for analyzing matter adhered to the inside wall of a vessel. Diseases such as arteriosclerosis occurs due to adhesion of matter, such as cholesterol ester, fatty acid and protein, to the inside wall of a vessel. A medical treatment for such diseases is different depending on what is the adhered matter. So, only if it can be found easily what is the matter adhered to the inside wall of a vessel, it will be of great help to the treatment of such diseases.

SUMMARY OF THE INVENTION

The present invention has been accomplished in view of the above situation. According to a first feature of the present invention, there is provided an analysis system of matter adhered to an inside wall of a vessel comprising a guiding apparatus and a Raman analysis apparatus; the guiding apparatus including a main body portion, a flexible insert portion extending from the main body portion and having a window formed in a distal end thereof, and a channel extending through the main body portion and insert portion and reaching the window, the insert portion being able to be inserted into the vessel; the Raman analysis system including a flexible insert cable to be inserted into the channel and whose distal end is faced with the window, an excitation optical fiber and a light receiving optical fiber which are both received in the insert cable, a light source connected to a basal end of the excitation optical fiber, and a spectroscope connected to a basal end of the light receiving optical fiber; and an excitation light emitted from the light source being projected through the window via the excitation optical fiber and Raman scattered by impinging on the matter adhered to the inside wall of the vessel, the scattered light being made incident to the window and spectrally analyzed by the spectroscope via the light receiving optical fiber, and thus the matter adhered to the inside wall of the vessel being analyzed.

By virtue of the above feature, a suitable medical treatment can be conducted depending on what is the adhered matter.

According to a second feature of the present invention, in the first feature, the Raman analysis apparatus includes a single number of the excitation optical fiber and a plural number of the light receiving optical fibers; and at a distal end portion of the insert cable, the single number of excitation optical fiber is arranged at a central area thereof and the plural number of light receiving optical fibers are arranged in such a manner as to surround the excitation optical fiber.

By virtue of this second feature, since only a single number of excitation optical fiber is employed in the Raman analysis apparatus, the insert portion of the insert cable and thus of the guiding apparatus can be made narrow so as to be easily inserted into the vessel. Also, it can be prevented that the light amount of the excitation light is increased, thus enabling to prevent the interior tissue structure of a patient's body from getting injured. On the other hand, since a plural number of light receiving optical fibers are employed, the Raman scattered light can surely be captured and transmitted to the spectroscope. Moreover, since the light receiving optical fibers are arranged in such a manner as to surround the excitation optical fiber, the Raman scattered light can more surely be captured.

According to a third feature of the present invention, in the second feature, the insert cable is provided at the distal end with a transparent light receiving plate having a center hole and against which distal ends of the plural number of light receiving optical fibers are abutted, and with a transparent excitation small piece fitted into the center hole and against which a distal end of the excitation optical fiber is abutted; a film-like excitation optical filter for cutting all of the excitation light only excepting a light having a predetermined wavelength is adhered to a surface of the excitation small piece which is faced with the excitation optical fiber; and a film-like light receiving optical filter for cutting only the light having a predetermined wavelength is adhered to a surface of the light receiving plate which is faced with the light receiving optical fibers.

By virtue of this third feature, an unnecessary constituent of the light can be cut by the optical filter, thus enabling to more easily make a spectral analysis by the spectroscope. Moreover, the distal ends of the optical filter and the optical fiber(s) can be protected with the light receiving plate and the excitation small piece, thus enabling to prevent the peel-off of optical filter. In addition, since the attachment member (excitation small piece) of the excitation optical filter and the attachment member (light receiving plate) of the light receiving optical filter are separately provided, those optical filters can surely be arranged separately.

According to a fourth feature of the present invention, in the first feature, the Raman analysis apparatus includes a single number of the excitation optical fiber and a plural number of the light receiving optical fibers; and the plural number of light receiving optical fibers are bundled at a distal end of the insert cable, the excitation optical fiber is arranged at an outer side in a radial direction of the bundle of light receiving optical fibers, and an optical means for deflecting an optical axis of the excitation light in a direction intersecting a center axis of the bundle of light receiving optical fibers is disposed at a distal end of the excitation optical fiber.

By virtue of this fourth feature, as in the case with the second feature, since only a single number of excitation optical fiber is employed and a plural number of light receiving optical fibers are employed, the insert cable can be made narrow, the light amount of the excitation light can be prevented from increasing and the Raman scattered light can surely be captured so as to be transmitted to the spectroscope. Moreover, since the excitation light is emitted in a slantwise direction towards the axis of the light receiving optical fibers bundle, the excitation light can surely be impinged on the adhered matter irrespective of the thickness of the matter adhered to the inside wall of the vessel. Thus, the Raman scattered light can surely be captured.

According to a fifth feature of the present invention, in the fourth feature, a distal end face of the excitation optical fiber is slanted with respect to an axis of the excitation optical fiber and the distal end face is provided as the optical means.

By virtue of this fifth feature, since the distal end face of the excitation optical fiber also serves as the optical means, the number of components can be reduced.

According to a sixth embodiment of the present invention, in the first feature, a film-like excitation optical filter for cutting all of the excitation light only excepting a light having a predetermined wavelength is adhered to a distal end face of the excitation optical fiber, and a film-like light receiving optical filter for cutting only the light having a predetermined wavelength is adhered to a distal end face of the light receiving optical fiber.

By virtue of this sixth feature, as in the case with the third feature, an unnecessary constituent of the light can be cut by the optical filter, thus enabling to more easily make a spectral analysis by the spectroscope. Moreover, since the optical filter is attached directly to the distal end face of the optical fiber, the number of components can be reduced.

According to a seventh feature of the present invention, in the first feature, excitation optical filters for cutting all of the excitation light only excepting a light having a predetermined wavelength are each disposed between the excitation optical fiber and the light source and disposed at a distal end face of the excitation optical fiber, respectively and a light receiving optical filter for cutting only the light having a predetermined wavelength is disposed at a distal end face of the light receiving optical fiber.

By virtue of this seventh feature, since the excitation light is subjected to the excitation optical filter at the basal end and distal end of the excitation optical fiber, an unnecessary constituent can more surely be cut. Thus, the spectral analysis can more easily be performed by the spectroscope.

According to an eighth feature of the present invention, in the first feature, the guiding apparatus is an endoscope through which an interior of the vessel can be observed.

By virtue of this eighth feature, the adhered matter can be found through the endoscope and the excitation light can surely be impinged on the adhered matter so as to facilitate an easy analysis of the adhered matter.

DETAILED DESCRIPTION OF THE INVENTION

Figure 1:
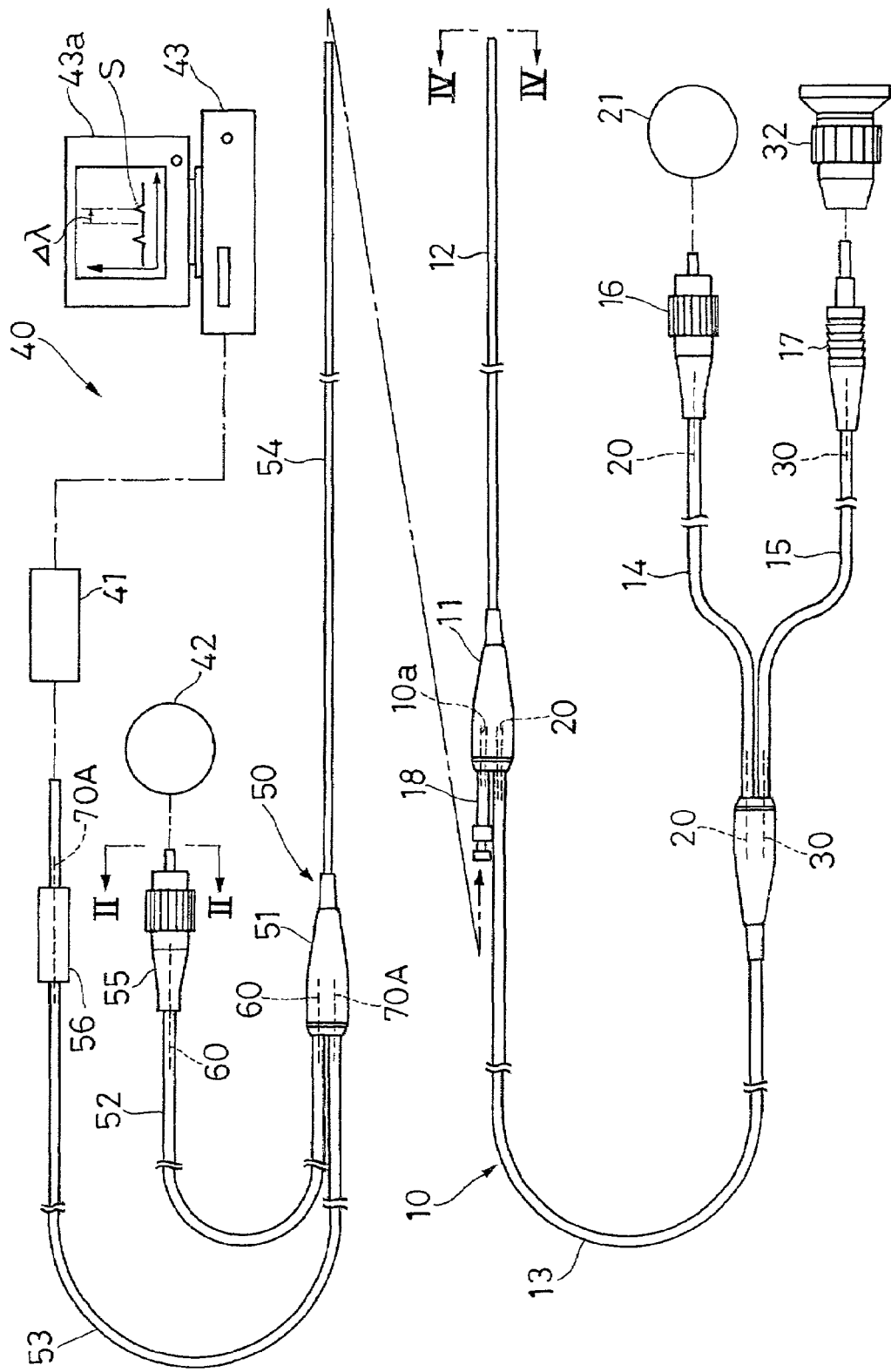
FIG. 1 is a side view of an analysis system according to a first embodiment of the present invention in which its endoscope and Raman analysis apparatus are shown in separated positions.

Several embodiments of the present invention will be described hereinafter with reference to the accompanying drawings. FIG. 1 shows an analysis system according to a first embodiment of the present invention. This analysis system comprises an endoscope 10 (guiding apparatus) and a Raman analysis apparatus 40.

The endoscope 10 will now be described.

Figure 5:
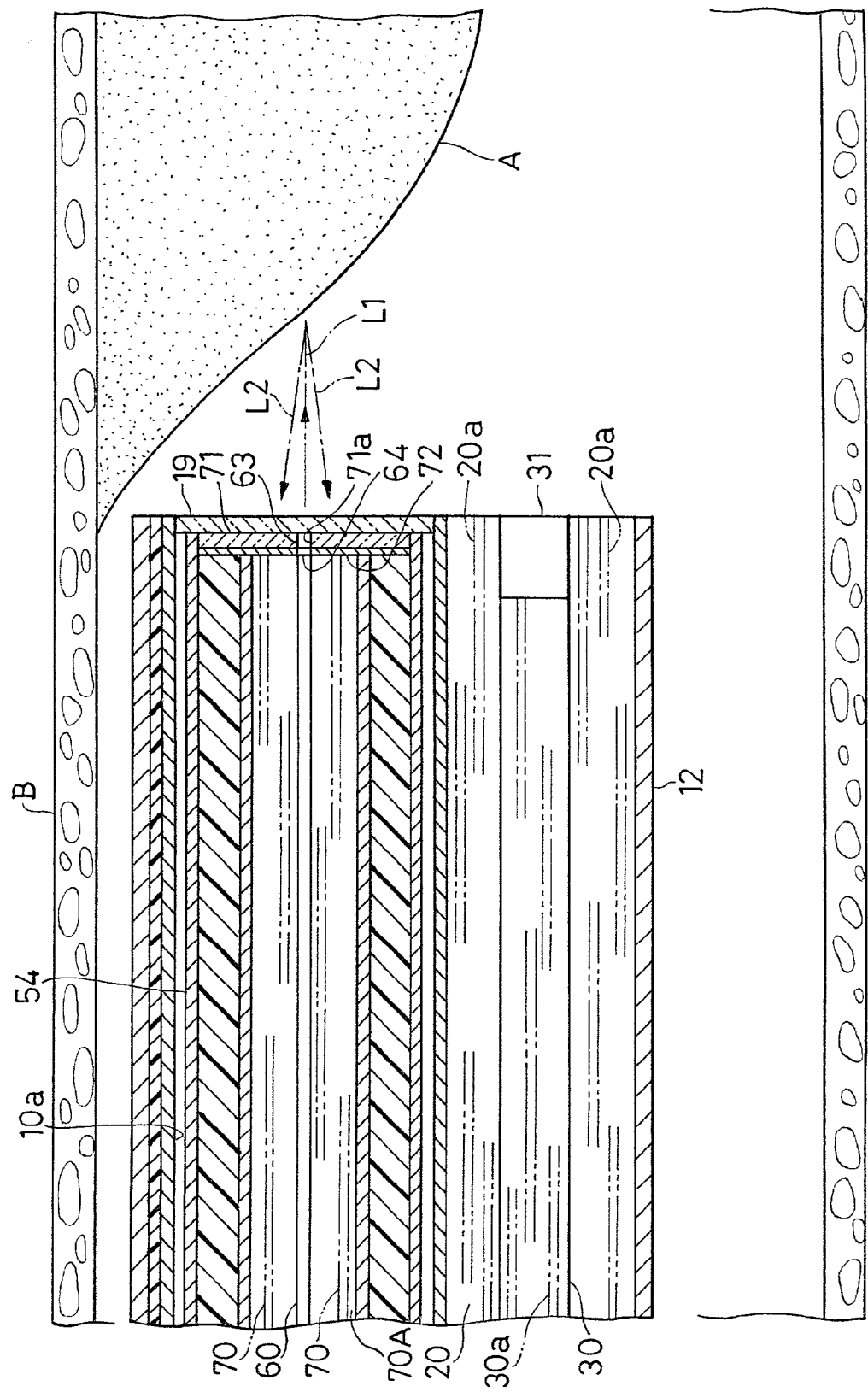
FIG. 5 is a sectional view, taken on line V—V of FIG. 4, of the analysis system which is in a condition of use.

The endoscope 10 includes a grip 11 (main body portion) and a flexible insert portion 12 extending from the grip 11. The outside diameter of the insert portion 12 is smaller, for example, 3.0 mm, than the inside diameter of a vessel B (FIG. 5).

An optical transmission system of the endoscope 10 will now be described. The grip 11 has a common cable 13 continuous with a basal end thereof A light cable 14 and an image cable 15 are branched from this common cable 13.

Figure 4:
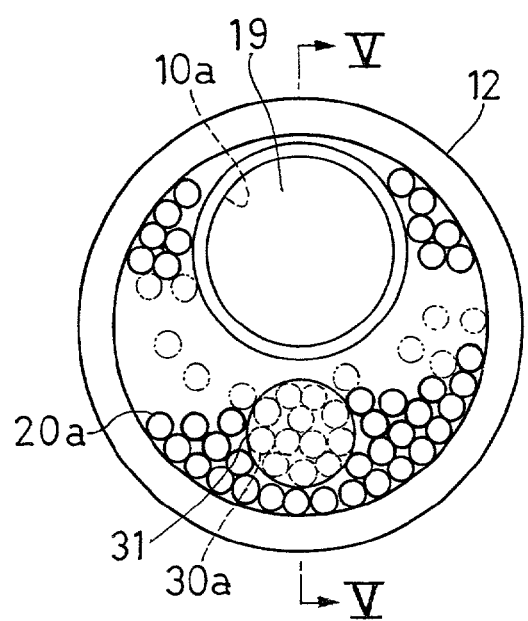
FIG. 4 is a view of a distal end of an insert portion of the endoscope taken on and viewed in a direction along line IV—IV of FIG. 1.

The light cable 14 is connected to an illumination light source 21 through a light plug 16. As shown in FIGS. 1, 4 and 5, a light guide 20 composed of a plurality of optical fibers 20a is received in the light plug 16, the light cable 14, the common cable 13, the grip 11 and the insert portion 12. A distal end of the light guide 20 is faced with an opening formed in a distal end of the insert portion 12.

A cylindrical Selfoc (Registered Trademark) lens 31 (objective lens) is disposed at the distal end of the insert portion 12 in such a manner as to be surrounded by the light guide 20. A distal end face of an image guide 30 composed of a plurality of optical fibers 30a is bonded to a basal end face of the Selfoc lens 31. The image guide 30 is received in the insert portion 12, the grip 11, the common cable 13 and the image cable 15 and reaches an image connector 17. An eye piece 32 having an ocular lens (not shown) is connected to the image connector 17. (In FIG. 4, the cross-sectional size, i.e. diameter, of the optical fibers 20a, 30a is exaggeratedly illustrated.) A channel 10a composed of a tube is formed in the grip 11 and insert portion 12 of the endoscope 10. A basal end of the channel 10a is continuous with the introducing pipe 18 (forceps mouth pipe) disposed at the grip 11, and a distal end thereof reaches the distal end of the insert portion 12. A transparent window glass 19 is disposed at a distal end opening (window) of the channel 10a. The inside diameter of the channel 10a is, for example, 1.5 mm.

The Raman analysis apparatus 40 will be described next.

As shown in FIG. 1, the Raman analysis apparatus 40 includes an excitation light source 42 for emitting a laser beam (excitation light), a spectroscope 41 for spectrally analyzing light, and a cable unit 50 connected to the light source 42 and the spectroscope 41. A personal computer 43 is connected to the spectroscope 41. The personal computer 43 converts the result of analysis made by the spectroscope 41 into a digital signal and is taken it therein so as to be displayed on a display 43a.

The cable unit 50 includes a grip 51, an excitation cable 52 and a light receiving cable 53 which are continuous with a basal end of the grip 51, and a flexible insert cable 54 continuous to a distal end of the grip 51. The excitation cable 52 is connected to the excitation light source 42 through an excitation connector 55, and the light receiving cable 53 is connected to the spectroscope 41 through a light receiving connector 56.

The outside diameter of the insert cable 54 is smaller (for example, 1.3 mm) than the inside diameter of the channel 10a of the endoscope 10, so that the insert cable 54 can be inserted into the channel 10a. As shown in FIG. 5, when the insert cable 54 is inserted into the channel 10a until its distal end comes into abutment with the window glass 19, the grip 51 is brought into abutment with the pipe 18 of the endoscope 10.

Figure 2:
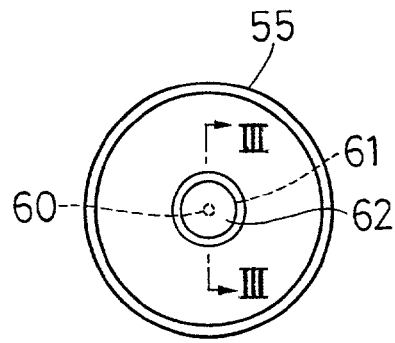
FIG. 2 is a view in which an excitation connector of the Raman analysis apparatus is taken on and viewed in a direction as indicated by arrow line II—II of FIG. 1.
Figure 3:
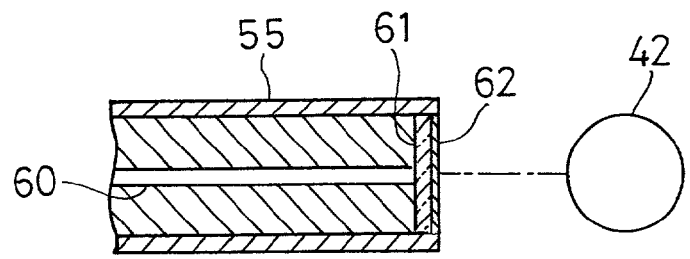
FIG. 3 is a sectional view of the excitation connector taken on line III—III of FIG. 2.

An optical transmission system of the cable unit 50 will now be described. A single number of excitation optical fiber 60 is received in the excitation connector 55, the excitation cable 52, the grip 51 and the insert cable 54. As shown in FIGS. 2 and 3, a basal end of the optical fiber 60 is abutted against a transparent glass plate 61 (excitation plate) disposed at the excitation connector 55. A film-like band pass filter 62 (excitation optical filter) is vapor deposited on a surface of the glass plate 61 which is faced with the light source 62. The band pass filter 62 cuts all of the laser beam emitted from the light source 42 only excepting a laser beam having a predetermined wavelength. (In the illustration, the diameter of the optical fiber 60 and the thickness of the filter 62 are exaggeratedly shown. The same shall be applied to an optical fiber 70 and filters 64, 72 as later described.)

As shown in FIG. 5, the distal end of the optical fiber 60 reaches a distal end portion of the insert cable 54.

A transparent glass plate 71 (light receiving plate) having a center hole 71a is fitted in the distal end opening of the insert cable 54, and a transparent small glass piece 63 (excitation small piece) is fitted in the center hole 71a. A band pass filter 64 (excitation optical filter) is vapor deposited on a surface on the back side (left side of FIG. 5) of the small glass piece 63. This band pass filter 64 also cuts all of the light only excepting a light having a predetermined wavelength as in the case with the band pass filter 62. The distal end of the optical fiber 60 is abutted against the small glass piece 63 through the filter 64.

On the other hand, a notch filter 72 (light receiving optical filter) is vapor deposited on the back side surface of the glass plate 71. This notch filter 72 cuts only the light having a predetermined wavelength.

As shown in FIGS. 1 and 5, a bundle 70A of a plural number of light receiving optical fibers 70 is received in the insert cable 54, the grip 51 the light receiving cable 53 and the light receiving connector 56. As shown in FIG. 5, those light receiving optical fibers 70 are arranged at the distal end portion of the insert cable 54 in such a manner as to surround the excitation optical fibers 60 (the excitation optical fiber 60 is arranged at the center of the light receiving optical fibers bundle 70A). The distal end of the optical fibers bundle 70A is abutted against the guide plate 71 through the notch filter 72.

A method of use of the analysis system thus constructed will now be described.

The insert portion 12 of the endoscope 10 is inserted into the vessel B, the illumination light coming from the illumination light source 21 is emitted through the light guide 20 in order to illuminate the interior of the vessel B. An image of the interior of the vessel B thus illuminated is transmitted to the ocular lens of the eye piece 32 via the Selfoc lens 31 and the image guide 30. By looking through the eye piece 32, the matter A adhered to the inside wall of the vessel B can be found.

After finding the adhered matter A, the insert cable 54 of the Raman analysis apparatus 40 is inserted into the channel 10a until it is abutted against the window glass 19. (The insert portion 12 may be inserted into the vessel B in a condition that the insert cable 54 is preliminarily inserted.)

Then, the illumination light source 21 of the endoscope 10 is turned off and the excitation light source 42 of the Raman analysis apparatus 40 is turned on. By doing so, a laser beam is emitted from the light source 42. After all the constituents only excepting a predetermined wavelength is cut at the band pass filter 62, the laser beam is transmitted through the excitation optical fiber 60. There is a possibility that Raman scatter occurs to the laser beam during the time the laser beam is transmitted through the excitation optical fiber 60. However, this Raman scattered light is cut during the time it passes through the band pass filter 64 at the distal end of the optical fiber 60. By this, only the laser beam having a predetermined wavelength passes through the small glass piece 63 and the window glass 19 and impinges on the adhered matter A, as indicated by an optical axis L1 of FIG. 5.

A part (about one ten thousandth of the whole) of the laser beam impinging on the adhered matter A raises Raman scatter and the wavelength is shifted. The shifting amount Δ λ (see the screen of the display 43a of FIG. 1) is determined by the compositions of the matter A. As indicated by L2 of FIG. 5, the Raman scattered light thus shifted in wavelength and the scattered light of the laser beam still having the predetermined wavelength are made incident to the window glass 19. Then, the scattered light still having the predetermined wavelength is cut during the time it passes through the notch filter 72 via the glass plate 71. By this, only the Raman scattered light is transmitted through the light receiving optical fibers 70. Although the Raman scattered light sometimes raises further Raman scatter during the time it is transmitted through the optical fibers 70, the light amount of the secondary Raman scattered laser beam is negligibly small.

The Raman scattered light transmitted via the light receiving optical fibers 70 is made incident to the spectroscope 41 and spectrally analyzed. The result of analysis is transmitted to the personal computer 43 and displayed on the display 43a in the form of a graph in which, for example, the wavelength is plotted along the abscissa and the intensity of the spectrum is plotted along the ordinate. Based on the shifting amount Δ λ from the predetermined wavelength of the spectrum S shown in the graph, it can be found what is the adhered matter A. Based on this finding, a suitable medical treatment can be conducted depending on what is the adhered matter A.

Further embodiments of the present invention will be described next. Like components of the first embodiment are denoted by like reference numerals in the following embodiments and description thereof is omitted.

Figure 6:
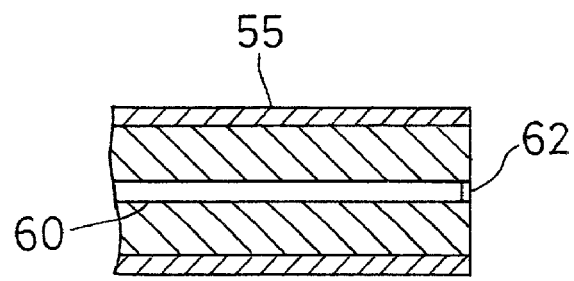
FIG. 6 shows a second embodiment of the present invention and is a sectional view of an excitation connector of a Raman analysis apparatus.

FIG. 6 shows a second embodiment of the present invention. In this second embodiment, the glass plate 61 is not disposed at the excitation connector 55 of the Raman analysis apparatus 40. The band pass filter 62 is vapor deposited on the basal end face of the excitation optical fiber 60.

Figure 7:
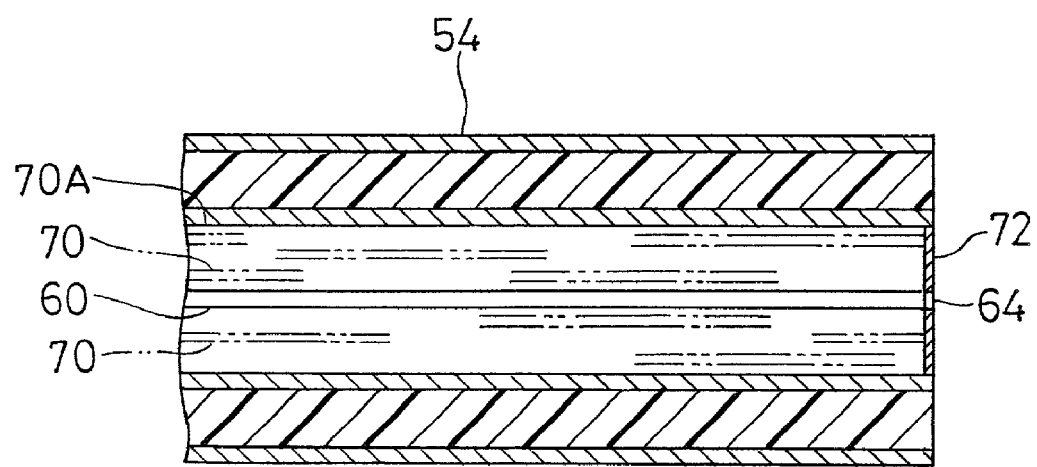
FIG. 7 shows a third embodiment of the present invention and is a sectional view of a distal end portion of an insert cable of a Raman analysis apparatus.

FIG. 7 shows a third embodiment of the present invention. In this third embodiment, the glass plate 71 and the small glass piece 63 are not disposed at the distal end of the insert cable 54. The band pass filter 64 is vapor deposited on the distal end face of the excitation optical fiber 60 and the notch filter 72 is vapor deposited on the distal end face of the light receiving optical fibers bundle 70A.

Figure 8:
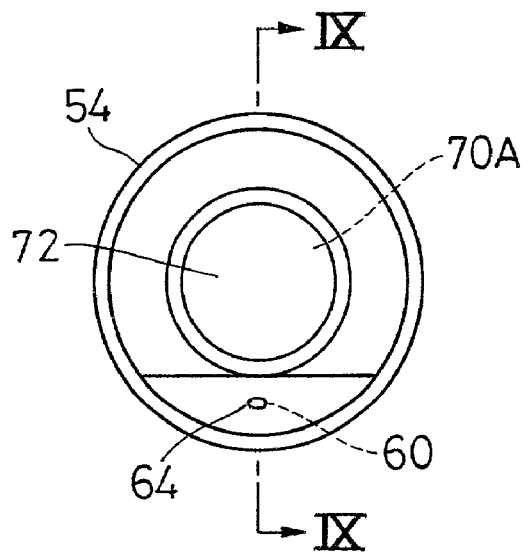
FIG. 8 shows a fourth embodiment of the present invention and is a front view of a distal end portion of a Raman analysis apparatus.
Figure 9:
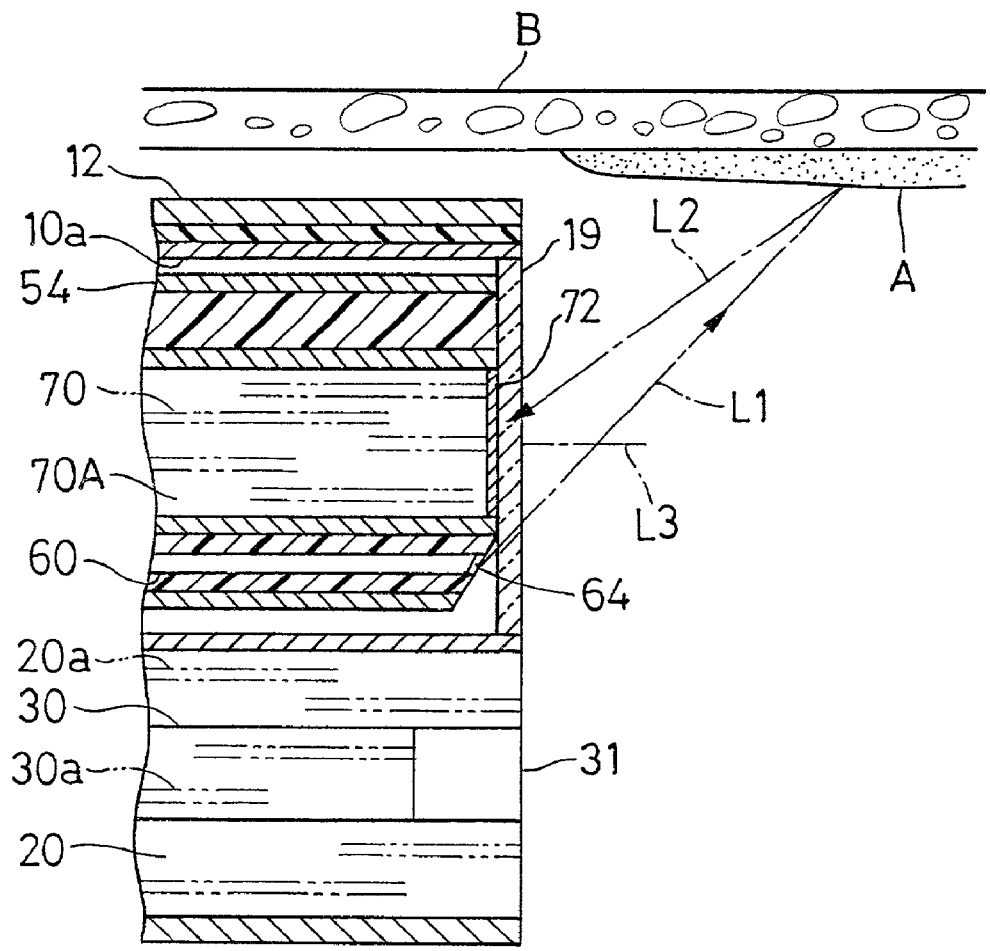
FIG. 9 is a sectional view, taken on line IX—IX of FIG. 8, of the analysis system of the fourth embodiment which is in a condition of use.

FIGS. 8 and 9 show a fourth embodiment of the present invention. In this fourth embodiment, the excitation optical fiber 60 is arranged on an outer side in a radial direction of the light receiving optical fibers bundle 70A at the distal end portion of the insert cable 54. The distal end face (optical means) of the excitation optical fiber 60 and the distal end face of the insert cable 54 in the peripheral area of the optical fiber 60 are slanted with respect to the optical axis of the excitation optical fiber 60. Owing to this arrangement, the laser beam is refracted at the distal end face of the excitation optical fiber 60 and the optical axis L1 of the laser beam after refracted, is refracted in a direction intersecting the axis L3 of the light receiving optical fibers bundle 70A. By this, even in the case where the adhered matter A is thin, the laser beam can surely be impinged on the adhered matter A and the raised Raman scattered light L2 can surely be taken into the light receiving optical fibers bundle 70A. The band pass filter 64 is vapor deposited on the distal end face of the excitation optical fiber 60 and a notch filter 72 is vapor deposited on the distal end face of the light receiving optical fiber bundle 70A.

The present invention should not be limited to the above embodiments. Instead, many changes and modifications can be made in accordance with necessity.

For example, a catheter can be used as the guiding apparatus. The window formed in the distal end of the insert portion of the guiding apparatus may be open.

What is claimed is:

1. An analysis system of matter adhered to an inside wall of a vessel comprising:

a guiding apparatus including a main body portion, a flexible inset portion extending from said main body portion and being able to be inserted said vessel and having a window formed in a distal end thereof, and a channel extending through said menu body portion and insert portion and reaching said window, and a Raman analysis apparatus including a light source emitting an excitation light, a spectroscope spectrally analyzing said matter adhered to the inside wall of said vessel, a flexible insert cable to be inserted into said channel and whose distal end is faced with said window, an excitation optical fiber being received in said insert cable and whose basal end is connected to said light source for transmitting said excitation light and whose distal end is arranged at a central area of the distal end portion of said insert cable, a plural number of light receiving optical fibers being received in said insert cable and whose basal end are connected to said spectroscope and whose distal end are arranged in such a manner as to surround said excitation optical fiber at the distal end portion of said insert cable, a transparent excitation small piece having a film-like excitation optical filter adhered to a surface thereof and the surface being abutted against a distal end of said excitation optical fiber, said film-like excitation optical filter cutting all light only excepting a light having a predetermined wavelength, and a transparent light receiving plate having a film-like light receiving optical filter adhered to a surface thereof and the surface being abutted against distal ends of said plural number of light receiving optical fibers, said film-like light receiving optical filter cutting only a light having said predetermined wavelength, wherein said excitation light along said excitation optical fiber is projected through said window and Raman scattered by impinging on said matter adhered to the inside wall of said vessel, said scattered light is made incident to said window, and said incident light is transmitted along said light receiving optical fibers to said spectroscope for analyzing, and wherein said transparent light receiving plate has a center hole and said transparent excitation small piece is fitted into said center hole.

2. An analysis system of matter adhered to an inside wall of a vessel according to claim 1, wherein another excitation optical filter for cutting all light only excepting a light having said predetermined wavelength is disposed between said light source and said excitation optical fiber.

3. An analysis system of matter adhered to an inside wall of a vessel according to claim 1, wherein said guiding apparatus is an endoscope through which an interior of said vessel can be observed.

* * * * *

UNITED STATES PATENT AND TRADEMARK OFFICE
CERTIFICATE OF CORRECTION

PATENT NO. : 6,970,736 B2
DATED : November 29, 2005
INVENTOR(S) : Komachi et al.

It is certified that error appears in the above-identified patent and that said Letters Patent is hereby corrected as shown below:

<u>Title page,</u>
Item [57], ABSTRACT,
Line 6, replace "receivingoptical" with -- receiving optical --.
Line 9, replace "reciving" with -- receiving --.

<u>Column 7,</u>
Line 17, replace "inset" with -- insert --.
Line 18, replace "inserted said vessel" with -- inserted into said vessel --.
Line 20, replace "menu" with -- main --.

Signed and Sealed this

Fourth Day of April, 2006

JON W. DUDAS
*Director of the United States Patent and Trademark Office*